United States Patent
Farrar

(10) Patent No.: US 6,821,295 B1
(45) Date of Patent: Nov. 23, 2004

(54) FLARED CORONARY ARTERY BYPASS GRAFTS

(75) Inventor: David J. Farrar, Moraga, CA (US)

(73) Assignee: Thoratec Corporation, Pleasanton, CA (US)

(*) Notice: Subject to any disclaimer, the term of this patent is extended or adjusted under 35 U.S.C. 154(b) by 90 days.

(21) Appl. No.: 09/604,114

(22) Filed: Jun. 26, 2000

(51) Int. Cl.$^7$ .................................................. A61F 2/06

(52) U.S. Cl. ................... 623/1.31; 623/1.32; 623/1.44

(58) Field of Search ................................ 623/1.1, 1.15, 623/1.16, 1.3, 1.31, 1.49

(56) References Cited

U.S. PATENT DOCUMENTS

| | | | |
|---|---|---|---|
| 3,818,511 A | * | 6/1974 | Goldberg et al. ............ 623/1.3 |
| 3,958,557 A | | 5/1976 | Sharp et al. |
| 3,988,782 A | | 11/1976 | Dardik et al. |
| 4,120,837 A | | 10/1978 | Schäfer et al. |
| 4,173,689 A | * | 11/1979 | Lyman et al. .............. 623/1.49 |
| 4,474,972 A | | 10/1984 | Das et al. |
| 4,475,972 A | | 10/1984 | Wong |
| 4,604,762 A | | 8/1986 | Robinson |
| 4,675,361 A | | 6/1987 | Ward, Jr. |
| 4,731,073 A | | 3/1988 | Robinson |
| 4,759,757 A | * | 7/1988 | Pinchuk ...................... 623/1.1 |
| 4,861,830 A | | 8/1989 | Ward, Jr. |
| 4,938,740 A | | 7/1990 | Melbin |
| 4,955,899 A | | 9/1990 | Della Corna et al. |
| 4,957,508 A | * | 9/1990 | Kaneko et al. ............. 623/1.1 |
| 4,957,669 A | | 9/1990 | Primm |
| 4,990,131 A | | 2/1991 | Dardik et al. |
| 5,084,065 A | | 1/1992 | Weldon et al. |
| 5,104,402 A | | 4/1992 | Melbin |
| 5,116,360 A | * | 5/1992 | Pinchuk et al. ............. 623/1.1 |

(List continued on next page.)

FOREIGN PATENT DOCUMENTS

| | | |
|---|---|---|
| EP | WO9525466 | 9/1995 |
| EP | WO9529712 | 11/1995 |
| EP | WO9529713 | 11/1995 |
| EP | WO9529714 | 11/1995 |
| EP | WO9630060 | 10/1996 |
| EP | WO9702791 | 1/1997 |
| EP | WO9731590 | 9/1997 |
| EP | WO9731591 | 9/1997 |
| EP | WO9833453 | 8/1998 |

(List continued on next page.)

OTHER PUBLICATIONS

Stedman's Medical Dictionary 70, 71, 195, 391, 1483, and 1830 (27th Ed. 2000).

(List continued on next page.)

*Primary Examiner*—Julian W. Woo
(74) *Attorney, Agent, or Firm*—Baker Botts L.L.P.

(57) ABSTRACT

A bypass graft includes a tubular portion having an internal tubular diameter and a first end and a second end. The tubular portion has a central axis. A flared portion has an adjoining end, wherein the adjoining end of the flared portion is integrally formed on and is substantially concentric with the second end of the tubular portion, and a flared end, wherein the flared end has a flared end internal diameter, such that the internal flared end diameter is greater than the internal tubular diameter. The flared portion includes a circumferential skirt for surgical attachment of the graft to a patient's blood vessel. A method for manufacturing a bypass graft, includes the steps of providing a mandrel having a tubular portion and a flared end with a flared end central axis; forming a layer of polyurethane over the mandrel; drying the layer of polyurethane on the mandrel; forming a skirt edge around the flared end of the mandrel to form an opening at a predetermined angle to the flared end central axis; forming a second edge around the tubular portion of the mandrel, and removing the graft from the mandrel.

52 Claims, 7 Drawing Sheets

U.S. PATENT DOCUMENTS

| | | | |
|---|---|---|---|
| 5,133,742 A | | 7/1992 | Pinchuk |
| 5,151,105 A | | 9/1992 | Kwan-Gett |
| 5,443,497 A | | 8/1995 | Venbrux |
| 5,453,235 A | | 9/1995 | Calcote et al. |
| 5,464,449 A | | 11/1995 | Ryan et al. |
| 5,556,414 A | | 9/1996 | Turi |
| 5,591,195 A | | 1/1997 | Taheri et al. |
| 5,641,443 A | | 6/1997 | Calcote et al. |
| 5,683,449 A | * | 11/1997 | Marcade ............... 623/1.1 |
| 5,741,333 A | | 4/1998 | Frid |
| 5,799,524 A | | 9/1998 | Schäfer et al. |
| 5,922,019 A | * | 7/1999 | Hankh et al. .......... 623/1.1 |
| 5,989,287 A | * | 11/1999 | Yang et al. ........... 623/1.1 |
| 6,015,431 A | | 1/2000 | Thornton et al. |
| 6,517,570 B1 | * | 2/2003 | Lau et al. ............ 623/1.13 |
| 6,589,278 B1 | * | 7/2003 | Harris et al. ........ 623/1.31 |

FOREIGN PATENT DOCUMENTS

| | | |
|---|---|---|
| EP | WO9833638 | 8/1998 |
| EP | WO0010487 | 3/2000 |
| EP | WO0027897 | 5/2000 |
| GB | 2140438 | 11/1984 |

OTHER PUBLICATIONS

European Search Report, dated May 7, 2002.

D. Farrar, Development of Prosthetic Coronary Artery Bypass Graft, *Heart Surgery Forum,* Abstract (pp. 36–40) Mar. 2000.

M. Phaneuf et al. *Coating of Dacron vascular grafts with an ionic polyurethane*; Biomaterials 22 (2001) 463–469.

PurSil and CarboSil, www.polymertech.com/SiUr.htm (4 pgs), printed Jun. 4, 2000.

Toratec Laboratories Corp., *Thoratec Thoralon ® brochure* (2 pgs), dated Nov. 1999.

The Polymer Technology Group Incorporated, www.polymertech.com/Products.htm (2 pgs) printed Apr. 14, 2000.

Guide to Elast–Eon ™medical Polymers, www.elastomeric.com/material/guide.topolymers.html (1 pg), dated 999.

CardioTech International, Inc., *CT Biomaterials,* www.cardiotech–Inc.com/biomatr.htm (5 pgs), dated 1999.

* cited by examiner

FLARED CORONARY ARTERY BYPASS GRAFTS

BACKGROUND OF THE INVENTION

1. Field of the Invention

The present invention relates generally to vascular grafts having at least one flared end to facilitate anastomosis to a blood vessel, such as a vein or an artery, or between blood vessels. More particularly, the present invention relates to polymer grafts having at least one flared end, which forms a skirt or cuff to form an anastomosis with the aorta.

2. Description of Related Art

When a blood vessel becomes occluded, a vascular surgeon may restore proper blood flow by performing a surgical bypass procedure. In the medical treatment of patients with diseased arteries or veins, surgeons may replace or bypass the occluded vessel with prosthetic conduits, such as vascular grafts. Examples of such grafts have been made from a polyester fabric (e.g., Dacron® fabric), or polytetrofluro-ethylene (PTFE) fabric (e.g., Teflon® fabric). Fabrics woven or knitted of these polymers also have been used as patches or reinforcements. Known procedures for restoring proper blood flow include creation of a formal surgical incision and exposure of the blocked artery or vein. A prosthetic bypass graft or a natural vein then may be sutured to the occluded vessel both upstream and downstream of the occlusion in order to divert the flow of blood around the occlusion. Known grafts, however, may kink or collapse mechanically under a variety of circumstances, such as when the graft is bent during the contraction of the surrounding muscle or tissue, or when external pressure is applied to the graft when the graft recipient moves. In addition, small diameter vascular grafts, i.e., internal diameters less than about six (6) mm, have a tendency to become obstructed due to neointimal proliferation or thrombus formation.

A solution to these problems has consisted of the reinforcement of the walls of vascular grafts by the attachment of either discrete polymeric rings or of a continuous spiral of polymeric bands to a portion, albeit sometimes a small portion, of the exterior surface of the graft. A reinforcing member may be fixed over the graft component through a variety of means or methods. Such reinforcing members are described in U.S. Pat. No. 5,085,065, which is incorporated herein by reference. The means or methods chosen to accomplish the fixation affects to a certain degree the graft's compliance, and the resultant compliance of the reinforced graft assembly may vary between applications of the reinforcing member. In addition, compliance is adjustable by winding the fibers of a reinforcing member at an angle, which may enhance kink resistance.

Although it may be desirable to reinforce grafts to prevent kinking or collapse, it is also essential that the graft remain compliant. Natural blood vessels are compliant and can expand both radially and longitudinally as blood is pumped through them. Reinforcing members, however, may reduce the radial compliance or the longitudinal compliance, or both, of an artificial grafts. A non-compliant graft may reduce the pulsatile flow through the graft, thereby compromising the ability of the graft to function naturally to correct an occlusion. In addition to the method described above, compliance may be adjusted by varying the durometer hardness of the fibers from which the reinforcing member is made and of the base material for the graft. Nevertheless, known manufactured vascular grafts may exhibit limited compliance.

SUMMARY OF THE INVENTION

Therefore, a need has arisen for a compliant, kink-resistant, and easy to handle vascular graft, such as coronary artery bypass graft (CABG). It is a feature of a graft according to the present invention that it has at least one flared end. Because the diameter of blood vessels may vary between patients, as well as within each patient, it is desirable to have a vascular graft, which has a diameter on one end larger than that on the other end. It is an advantage of this flared end configuration that it facilitates surgical attachment of the graft to an artery, such as the aorta. It is a further advantage of this flared end configuration that the effects of neointimal proliferation may be reduced or eliminated, especially in small diameter vascular grafts. It is another feature of a graft according to the present invention that it may be made from polymeric materials, for example, polyurethanes, such as polyether urethanes, polycarbonate urethanes, polyester urethanes, silicone polyether urethanes, silicone polycarbonate urethanes, or the like. It is yet another feature of a graft according to the present invention that the side walls of the graft may be reinforced. In particular, the graft may be reinforced by a multi-layered construction.

Moreover, a graft according to the invention may be substantially cylindrical or tubular to attain increased graft strength and resistance to tearing, especially at connection points with an occluded and a bypass vein or artery. It is an advantage of the use of these polymeric materials that graft may be flexible and kink-resistant.

In an embodiment of the present invention, a bypass graft, such as a CABG, comprises a tubular portion having an internal tubular diameter and a first end and a second end. The tubular portion has a central axis. A flared portion has an adjoining end, wherein the adjoining end of the flared portion is integrally formed on and is substantially concentric with the second end of the tubular portion. The flared portion also has a flared end, wherein the flared end has an internal flared end diameter, such that the internal flared end diameter is greater than the internal tubular diameter; whereby the flared portion comprises a circumferential skirt for surgical attachment of the graft to a patient's blood vessel, i.e., a vein or an artery.

The present invention provides a graft having a first and a second end. The first end is flared around the central axis of the internal diameter of the graft to form a skirt having a substantially circular opening larger than the internal diameter, for surgical attachment of the first end to a blood vessel, such as the aorta. The skirt may alternatively be asymmetrically flared around the central axis of the graft forming a substantially elliptically shaped opening, The circular or elliptical opening of the skirt may have an axis which is parallel to the axis of the internal diameter of the graft or, alternatively, the axis of the skirt may be at an oblique or other angle to the axis of the internal diameter of the graft, so that it may be readily sutured at an acute angle. In either the circular or the elliptically (e.g., asymmetrically) flared configurations, the skirt is adjustable, trimmable, or foldable to be readily adapted for suturing at an acute angle to a vein or an artery, such as the aorta.

Methods for forming multi-layered, polyurethane, CABG are also provided by coating suitably shaped mandrels with polyurethane materials. In a further embodiment of this invention, a method for manufacturing a bypass graft, comprises the steps of providing a mandrel having a tubular portion and a flared end with a flared end central axis; forming at least one layer of polyurethane over the mandrel; drying the at least one layer of polyurethane on the mandrel;

forming a skirt edge around the flared end of the mandrel to form an opening at a predetermined angle to the flared end central axis; forming a second edge around the tubular portion of the mandrel; and removing the graft from the mandrel.

Other objects, features, and advantages will be apparent to those skilled in the art in view of the following detailed description of the drawings and the accompanying drawings.

BRIEF DESCRIPTION OF THE DRAWINGS

The present invention may be more readily understood with reference to the following drawings, in which.

DESCRIPTION OF PREFERRED EMBODIMENTS

Figure 1:
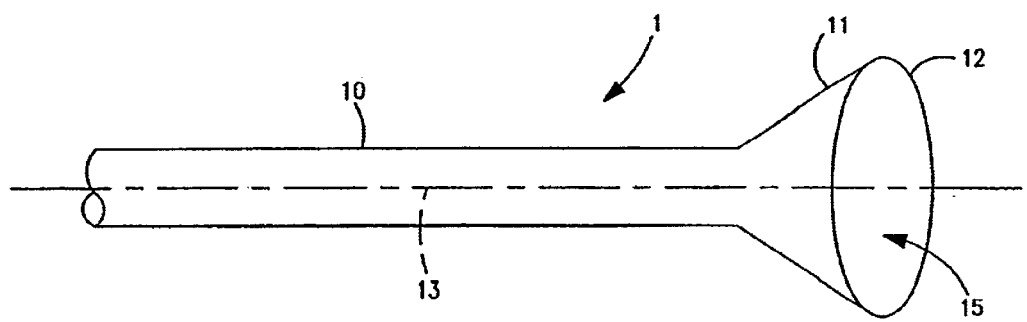
FIG. 1 depicts an embodiment of a graft having a flared end according to the invention.

FIG. 1 depicts a graft 1 according to the invention, namely a CABG, having a flared end. A tubular portion 10 of graft 1 has one flared end, formed by a skirt 11, which is symmetrically flared to form a substantially circular opening 12. The axis of opening 12 is substantially parallel to, if not concentric with, an axis 13 of the tubular portion 10. Thus, opening 12 may be substantially concentric with tubular portion 10. Skirt 11 forms an open space 15, which is circumferentially and volumetrically larger than the space provided in a corresponding section of the tubular portion 10. Preferably, graft 1 is monolithic, i.e., it is formed without intervening seams or overlap, whereby skirt 11 forms a continuous, integral, monolithic section of graft 1.

Figure 2:
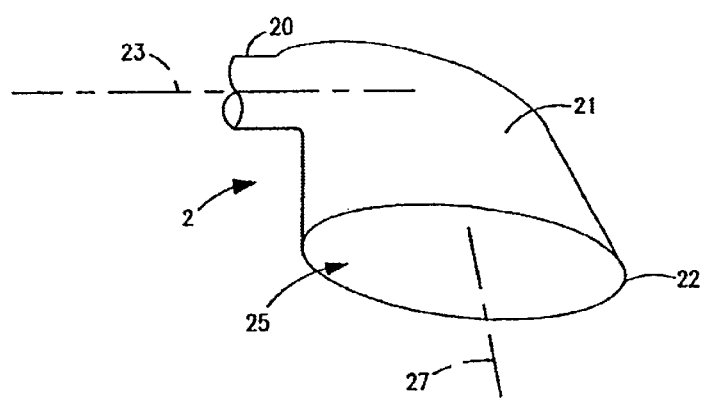
FIG. 2 depicts another embodiment of a graft having a flared end according to the invention.

FIG. 2 depicts another embodiment of a graft 2 having a flared end according to the invention showing only the flared end, which is modified compared to that shown in FIG. 1. A tubular portion 20 of graft 2 has one flared end, formed by a skirt 21, which is asymmetrically flared to form a substantially circular opening 22. An axis 27 of opening 22 forms an oblique angle, e.g., an angle greater than 0° and less than or equal to 90°, with an axis 23 of tubular portion 20. Thus, opening 22 may be substantially offset from tubular portion 20. Skirt 21 forms an open space 25, which is circumferentially and volumetrically larger than the space provided in a corresponding section of the tubular portion 20. Preferably, graft 2 is monolithic, i.e., it is formed without intervening seams or overlap, whereby skirt 21 forms a continuous, integral, monolithic section of graft 2.

The flared end forms a skirt 21 having opening 22, which is formed by asymmetrically flaring the end of graft 2. Central axis 27 of opening 22 is formed at an oblique angle to the central axis 23 of tubular portion 20 of graft 2. This angular relationship facilitates the grafting of the skirt 21 onto a blood vessel, e.g., a vein or an artery, at an acute angle.

Figure 3:
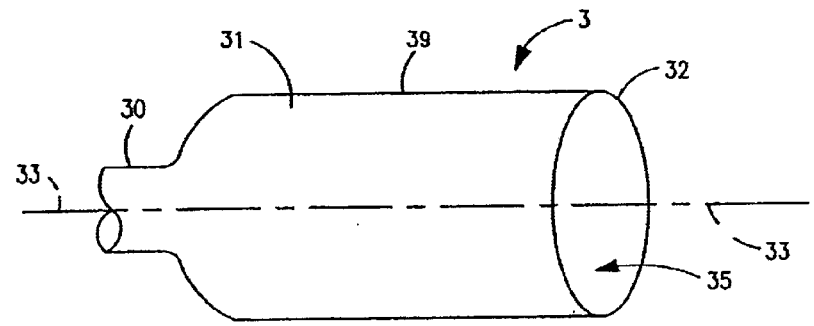
FIG. 3 depicts still another embodiment of a graft having a flared end according to the invention.

Referring to FIG. 3, a graft 3 is still another embodiment of the invention having a flared end, which is a further modification of the flared end of FIG. 1. A skirt 31 is extended to form an elongated skirt portion 39, thereby increasing the volume of the interior space defined by skirt 31 and elongated skirt portion 39. The axis of opening 32 is substantially parallel to, if not concentric with, an axis 33 of the tubular portion 30. Skirt 31 forms an open space 35, which is circumferentially and volumetrically larger than the space provided in a corresponding section of the tubular portion 30. Preferably, graft 3 is monolithic, i.e., it is formed without intervening seams or overlap, whereby skirt 31 forms a continuous, integral, monolithic section of graft 3.

Figure 4:
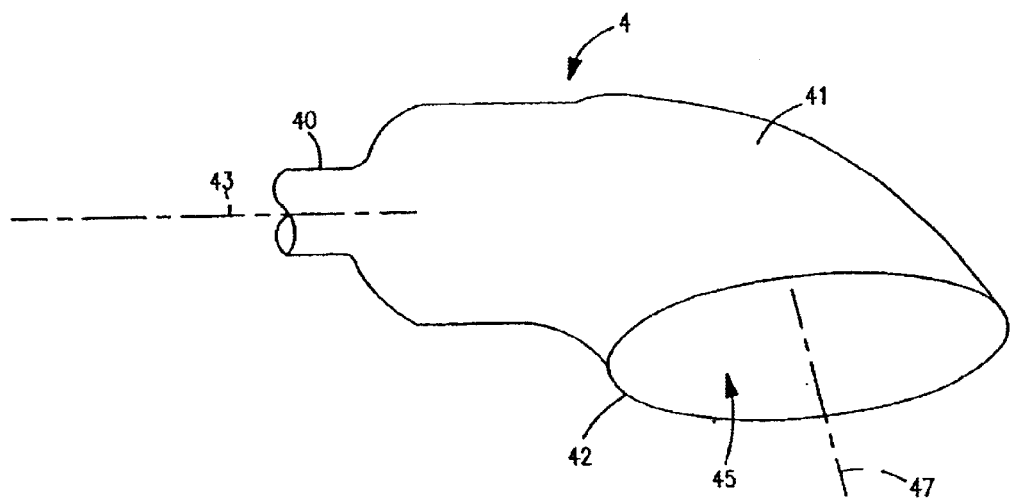
FIG. 4 depicts yet another embodiment of a graft having a flared end according to the invention.

Referring to FIG. 4, a graft 4 is yet another embodiment of the invention having a flared end, which is modified compared to that shown in FIG. 1. A tubular portion 40 of graft 4 has one flared end, which terminates with a skirt 41, which is asymmetrically flared to form a substantially circular opening 42. An axis 47 of opening 42 forms an oblique angle, e.g., an angle greater than 0° and less than or equal to 90°, with an axis 43 of tubular portion 40. Thus, opening 42 may be substantially offset from tubular portion 40. Skirt 41 forms an open space 45, which is circumferentially and volumetrically larger than the space provided in a corresponding section of the tubular portion 40. Preferably, graft 4 is monolithic, i.e., it is formed without intervening seams or overlap, whereby skirt 41 forms a continuous, integral, monolithic section of graft 4.

As noted above, the flared end forms a skirt 41 having opening 42, which is formed by asymmetrically flaring the end of graft 4. Central axis 47 of opening 42 is formed at an oblique angle to the central axis 43 of tubular portion 40 of graft 4. This angular relationship facilitates the grafting of the skirt 41 onto a blood vessel, e.g., a vein or an artery, at an acute angle.

Figure 5:
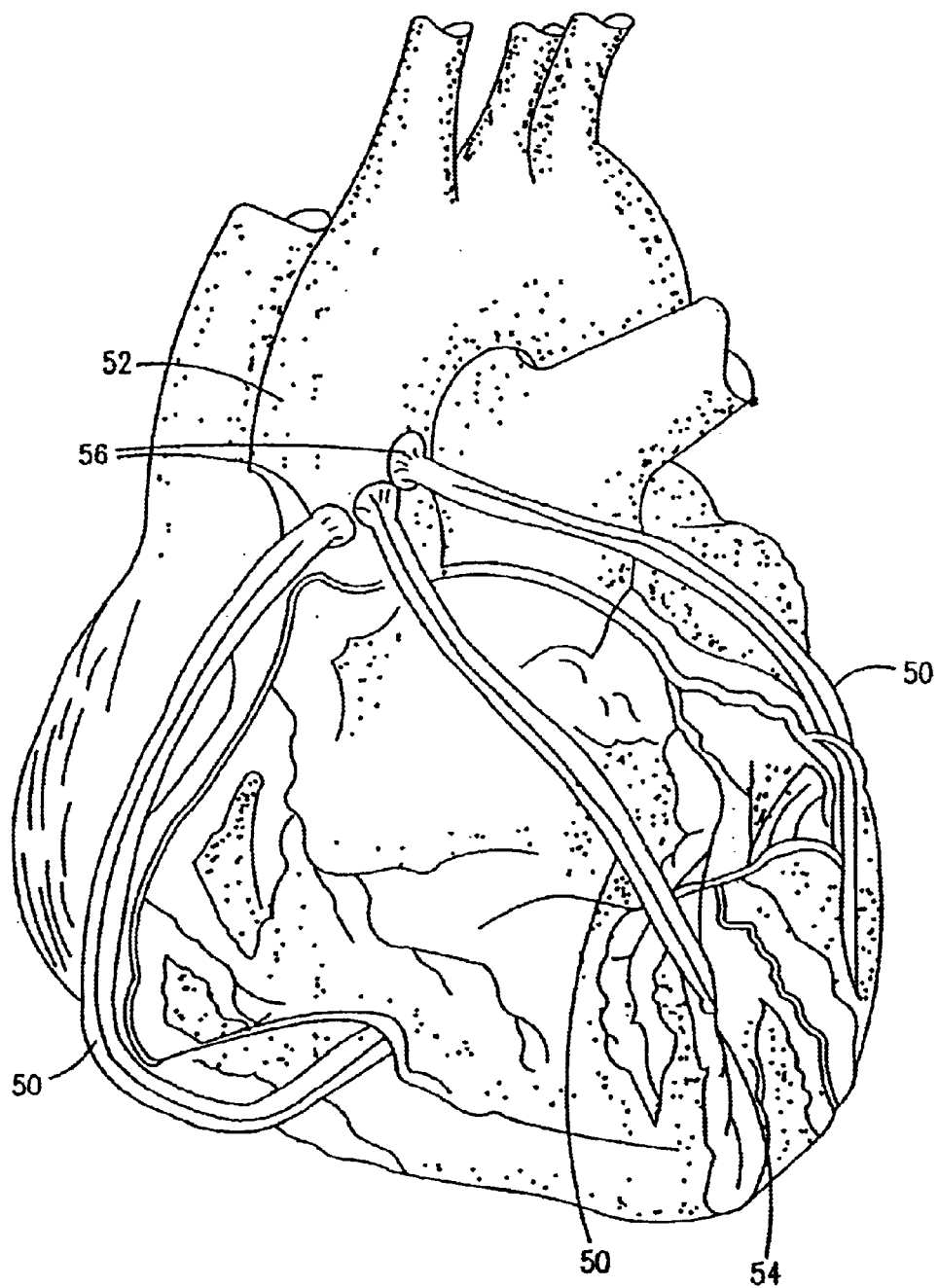
FIG. 5 shows the use of the flared CABG connecting the aorta to a coronary artery.

Referring to FIG. 5, a CABG 50 is shown, in which the flared end 56 of CABG 50 connects the aorta 52 to coronary artery 54. Flared ends 56 of grafts 50 are anastomosed to the aorta 52.

Figure 6:
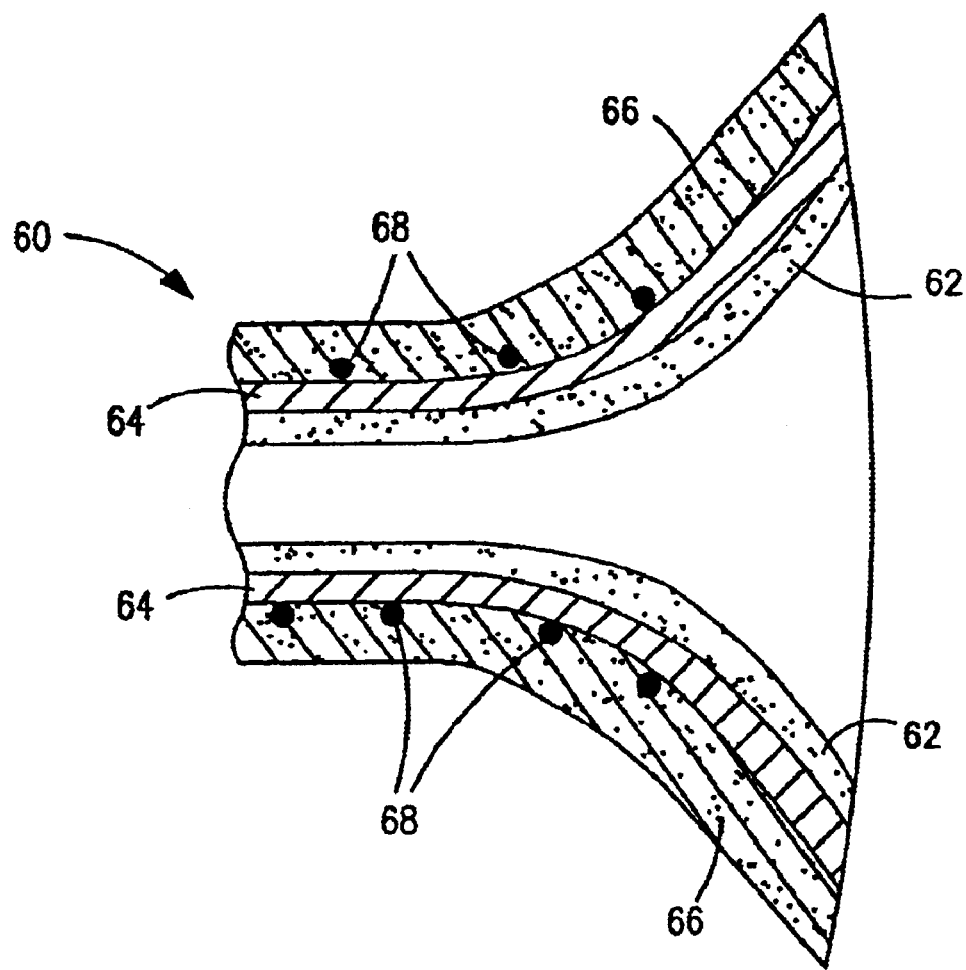
FIG. 6 is a cross-sectional view of the layered structure of the flared grafts according to the invention.

Referring to FIG. 6, the flared end of a partial cross-sectional view of a CABG according to the present invention is shown. Such a flared end may comprise at least three (3) structural zones. Such layered structural zones are described in detail in U.S. Pat. Nos. 4,605,762 and 4,731,073, which are incorporated herein by reference. A first interior microporous zone 62 is a polyurethane material adjacent to a second zone 64 of nonporous polyurethane elastomer. First zone 62 forms a microporous blood interface having pores with diameters in a range of about 5 to about 100 microns. The material of first zone 62 may be treated to become either hydrophillic or hydrophobic by known treatments, depending upon the use of the graft. Alternatively, first zone 62 may be made from a hydrophobic material, e.g., Biomer™ polymer material, especially, in small diameter grafts. If desired, the hydrophillic or hydrophobic microporous blood interface may be coated with an antithrombogenic, such as albumin, gelatin, glycoproteins, bonded heparin, or comparable material to prevent or diminish early thrombus formation.

Preferably, the polymer used to form first zone 62 has a low surface free energy or a high contact angle hysteresis, or both. Surface free energy may be measured by Zisman's critical surface tension, $\gamma_c$. Preferably, the surface free energy is in a range of about 20 to about $30 \times 10^{-5}$ N/cm. This combination of features allows the material of first zone 62 to exhibit the desirable qualities of flexibility, softness, and strength. Suitable polymer materials and admixtures for this and other zones are described in detail in U.S. Pat. Nos. 4,675,361 and 4,861,830, which are incorporated herein by reference.

Second zone 64 is an impervious zone, which may be formed from a segmented polyether polyurethane material. The term "segmented" refers to the relatively short length of a repeating unit, e.g., less than about ten (10) monomeric units, but preferably less than about three (3) monomeric units, typically alternating more than once. This material may be continuous and may form a barrier to blood within the normally encountered blood pressure ranges. In an embodiment, second zone 64 may have a radial thickness of about 40 to about 240 microns.

A third zone 66 also may contain reinforcing members 68 to prevent the collapse and kinking of the CABG. As with second zone 64, third zone 66 may be formed from segmented polyether-polyurethane. During the formation of this zone, however, salt particulates, such as sodium chloride particulates with an average diameter of less than about 38 microns and a range of diameters between about 15 and about 115 microns, may be used to form pores of corresponding sizes. In an embodiment, third zone 66 may have a radial thickness of about 400 to about 3200 microns.

Reinforcing member 68 may be made of a suitable filament, such as a wire, a polyethylene fiber, a solid elastomer, Kevlar® fiber, and the like. It is not necessary that reinforcing member 68 be limited to third zone 66 or to any single zone. Nevertheless, it is desirable that at least one of the zones is so reinforced. Reinforcing member 68 may be formed as a spiral about graft 60. The tensile elastic modulus of reinforcing member 68 is preferably in a range of about 68,947.57 to about 13,789,514 kPa (about 10,000 to about 2,000,000 psi). Moreover, the ratio of the distance between spiral loops, i.e., the pitch of the spiral, to the diameter of reinforcing member 68, is preferably in a range of about 1.5 to about 5.

Particularly for third zone 66, but also for first zone 62, the homogeneous pores are initially formed by the use of particulates of salt, such as sodium chloride or sodium bicarbonate. These salts are added to the polymer and are ultimately and largely removed by diffusion in a water or very dilute acid bath. If sodium bicarbonate is used, it also may act as a blowing agent, releasing $CO_2$ and thereby decreasing the amount of salt to be removed from the core of each pore. As noted above, the particulates used to form the pores are screened to afford a limited and somewhat narrow range of particulate diameters, so that the pores thus formed are limited to a narrow range of diameters. The result is a porous foam-like structure containing closed-cell or open-cell voids and having a substantially reduced density.

The salt particulates and the polymer solution are completely and homogeneously mixed to form a slurry, from which the graft layers (or zones) are formed. Moreover, different slurries, with or without salt particulates, then may be used to form various layers, such as the three zones described above, on a mandrel. As discussed below, the various layers may be applied until the graft is fabricated. The layers on the mandrel then may be thoroughly dried to remove the solvent, and the salt particulates then may be removed in a water or dilute acid bath at about 60° C.

While FIG. 6 shows the three zones of the graft separated by solid lines, these zones may be homogeneously joined to each other while the substance of at least one of the zones is in a liquid or semi-liquid state. The three zones may be formed from the same general material, such as polyurethane. The polyurethane may be dissolved in a solvent and applied as a viscous liquid. The solvent within the liquid penetrates the surfaces of the joined zones and provides homogeneous mixing of the polymers and adhesion as if it were of one material. Consequently, the interface between zones has some finite dimension of thickness, not shown in FIG. 6, but having a composition which is a blend of the two adjacent zones.

Figure 7A:
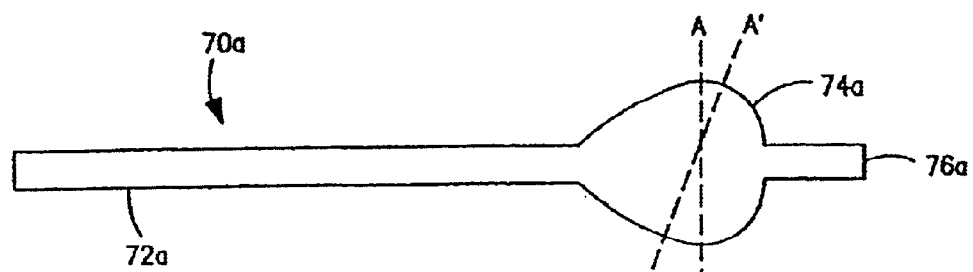
FIGS. 7a–c depict various mandrel configurations.
Figure 7B:
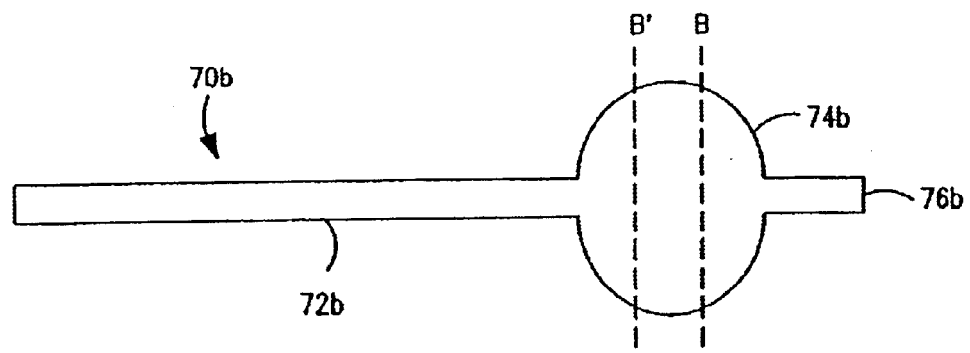
Figure 7C:
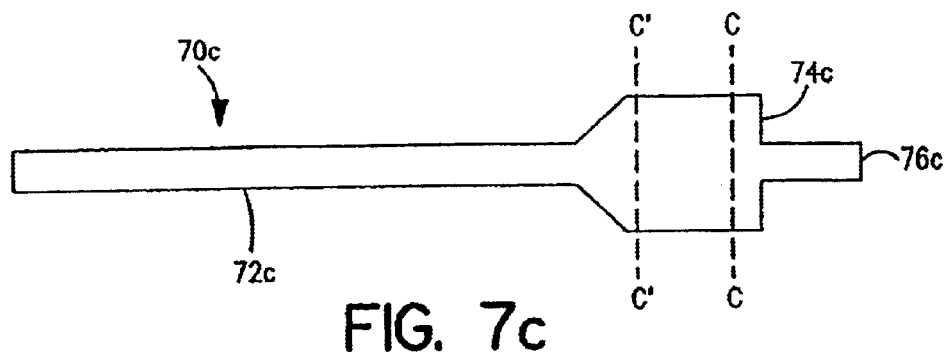

To form the grafts, such as CABGs, flared mandrels of suitable internal diameters are made, and the polyurethane compositions or slurries containing such polyurethane are applied to the surfaces of these mandrels. Referring to FIGS. 7a–c, such mandrels 70a–c may be made from glass, ceramic, metal, or another smooth surfaced material capable of receiving a polyurethane coating to form a graft and from which such a polyurethane graft may be removed without damage. Consequently mandrels 70a–c may be manufactured from a rigid, heat resistant material having a naturally non-stick surface or mandrels 70a–c may be made from a material coated with a suitable non-stick material, such as PTFE.

The shape of mandrels 70a–c is chosen to conform to the desired shape of the grafts. For example, mandrels 70a–c include a tubular portion 72a–c, respectively, on which the tubular portion of the grafts may be formed. A flared end bulb 74a–c may be formed at one end of tubular portion 72a–c, respectively. By applying polyurethane to bulb 74a–c, a flared end of the graft may be formed. While three bulb shapes are depicted in FIGS. 7a–c, it will be understood by persons skilled in the art that various bulb shapes are possible and that the bulb shape may be selected to achieve any desired flared end size and shape.

In addition, mandrels 70a–c may be further adapted for use in automated fabrication techniques an extension 76a–c is formed on bulb 74a–c, respectively. Extension 76a–c may be used to secure mandrel 70a–c while it is dipped in or drawn through a polyurethane composition or a slurry including a polyurethane composition. Alternatively, extension 76a–c may be used to suspend or to suspend and rotate mandrel 70a–c while a polyurethane composition is sprayed onto the surface of mandrel 70a–c.

As described above, the grafts are formed with a flared end opening having a diameter greater than that of the tubular portion. Referring to FIG. 7a, dashed lines A-A and A'-A' show that shape and the orientation of the flared end opening may be altered by cutting the graft at different angles on bulb 74a. Referring to FIG. 7b, dashed lines B-B and B'-B' show that the diameter of the flared end opening and the length of the skirt may be altered by cutting the graft at different positions on bulb 74b. Moreover, referring to FIG. 7c, dashed line C-C and C'-C' show that the length of the skirt of a graft, such as that described in FIG. 3, may be adjusted by cutting the graft at different positions on bulb 74c.

The polyurethane coatings may be applied to the mandrel surface by various methods, including drawing the mandrel through a polyurethane slurry, dipping the mandrel in a polyurethane slurry, or spraying the mandrel with a polyurethane slurry. Multiple layers of polyurethane may be applied by repeating the application process. The thickness of a polyurethane layer may be controlled by varying the length of time which the mandrel remains exposed to the source of polyurethane (e.g., the length of time for which the mandrel is dipped in or drawn through the source of polyurethane) or duration or rate of spraying, or both, to which the mandrel is subjected. The thickness of each polyurethane layer may be controlled by passing the dipped mandrel through dies, which limit the layer thickness. Flared ends are formed at one end before the graft is dry, as described below.

To form the micro-porous layers, homogenous pores may be initially formed by the use of soluble particulates, such as sodium chloride or sodium bicarbonate, which are eventually removed by diffusion in a water bath or dilute acid bath. The particulates utilized for this purpose are screened to afford a narrow range of sizes. The result is a porous or foam-like structure having closed voids or open voids, or both. Preferably, average the pore diameters are in the range of about 15 microns to about 115 microns. More preferably, the average pore diameter is less than about 38 microns.

Various slurries with or without particulates are formed and applied directly onto the mandrels by dipping or drawing. Each layer is sequentially formed by dipping into or drawn through a slurry including a source of polyurethane having a pre-selected combination of particulates and polymeric solids, until the entire graft is fabricated. The coatings on the mandrels then are dried thoroughly to remove the solvent, and the sodium chloride or sodium bicarbonate particles may be removed in a water bath or dilute acid bath at about 60° C. The particle size and concentration of particles are arranged to control the density or porosity and pore size. Preferably, the total void percentage of volume in a micro-porous layer is in a range of about 30% to about 90% of the total layer volume, still more preferably, the total void percentage may be about 50%.

To form the reinforcing member or a reinforced outer layer, a filament or wire may wound around the previously dried layer(s). A final dip or drawing may be used to coat the wire or filament to adhesively fix the reinforcement onto the catheter. Preferably, the material used to form the layers is a polyurethane. Such polyurethanes preferably are made from diphenylmethane diisocyanate (MDI), polytetramethylene oxide (PTMO) and a chain extender, such as an alkanediol or alkanediamine.

Various polymers may be used to form layers (or zones) of the graft. The graft may be made from a polymer selected from the group consisting of polyether urethanes, polycarbonate urethanes, polyester urethanes, and PHMO polyurethanes. For example, the polymer may be polyether urethanes, such as Thoralon® polymer material available from Thoratec Laboratories Corporation of Pleasanton, Calif., or Biospan® polymer material, available from The Polymer Technology Group, Inc. of Emeryville, Calif.; polycarbonate urethanes, such as Chronoflex® polymer material, available from Cardiotech International, Inc. of Woburn, Mass., or Bionate® polymer material, available from The Polymer Technology Group, Inc. of Emeryville, Calif.; silicone polyether urethanes or silicone polycarbonate urethanes, such as PurSil™ polymer material or Carbo-Sil™ polymeric material, respectively, available from The Polymer Technology Group, Inc. of Emeryville, Calif.; or PHMO polyurethanes, such as Elast-eon™ polymer material, available from Elastomedic Pty Ltd. of Chatsworth, New South Wales, Australia.

Figure 8:
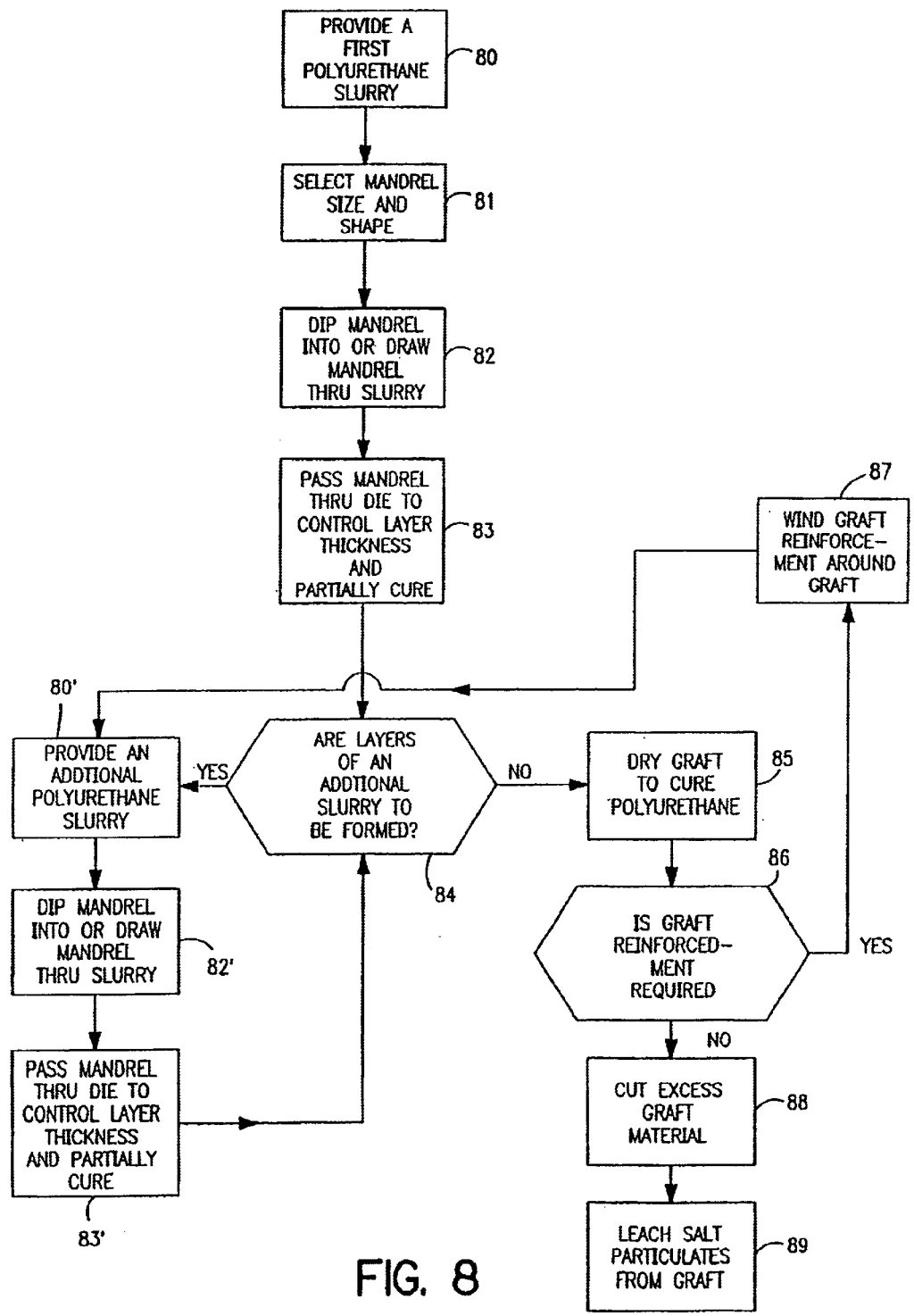
FIG. 8 is a flow chart of an embodiment of a method for forming grafts according to the invention.

Referring to FIG. 8, a flow chart depicts an embodiment of a method for forming grafts according to the invention. In step 80, a first slurry containing a polyurethane composition is provide, and in step 81, a mandrel is selected with a desired size and shape. In step 82, the mandrel then may be dipped into or drawn through the first slurry. This process may be repeated until the desired layer thickness is achieved. Further, masking may be applied to the mandrel to ensure that only a portion of the mandrel's surface is coated in polyurethane. In step 83, the mandrel may be passed through a die to adjust the thickness of the polyurethane layer, and the polyurethane layer is partially cured. This partial curing allows the formation of distinct layers using slurries comprising up to about 70% solvent.

In step 84, it is determined whether additional layers of polyurethane are to be applied to the mandrel. If so, in step 80', an additional polyurethane slurry is provided, and in steps 82' and 83', an additional layer is applied to the mandrel and the thickness of the additional layer may be adjusted by passing the mandrel through a die, and the polyurethane layer is partially cured.

Once the desired layers have been deposited on the mandrel (step 84), the polyurethane layers are dried (e.g., cured) in step 85. If the graft is to be reinforced (step 86), a graft reinforcement means, such as a wire or fiber, may be wound around the graft (step 87), and an additional coating of polyurethane may be applied over the graft reinforcement means (steps 80',82', and 83'). In step 88, excess graft material may be removed from the graft, and in step 89, salt particles may be leached from the graft to create the desired porous layer(s).

Alternatively, the various slurries described above may be applied directly onto the mandrels by spraying. Each layer is sequentially formed by spraying an appropriate slurry onto a mandrel until the entire graft is deposited on the mandrel. The coatings on the mandrels then are dried thoroughly to remove the solvent, and the sodium chloride or sodium bicarbonate particles may be removed (e.g., leached) in a water bath or dilute acid bath at about 60° C. As noted above, the particle size and concentration of particles are arranged to control the density or porosity and pore size. Preferably, the total percentage volume of voids or pores in a microporous layer is in a range of about 30% to about 90% of the layer volume, still more preferably, the total percentage volume of voids or pores may be about 50%.

To form the reinforcing member or a reinforced outer layer, a filament or wire may be wound around the previously dried layer(s). A final spraying or dipping may be used to coat the wire or filament to adhesively fix reinforcement onto the graft. As noted above, the material used to form the layers preferably polyurethane. Such polyurethanes preferably are made from diphenylmethane dilsocyanate (MDI), polytetramethylene oxide (PTMO) and a chain extender, such as an alkanediol or alkanediamine.

Figure 9:
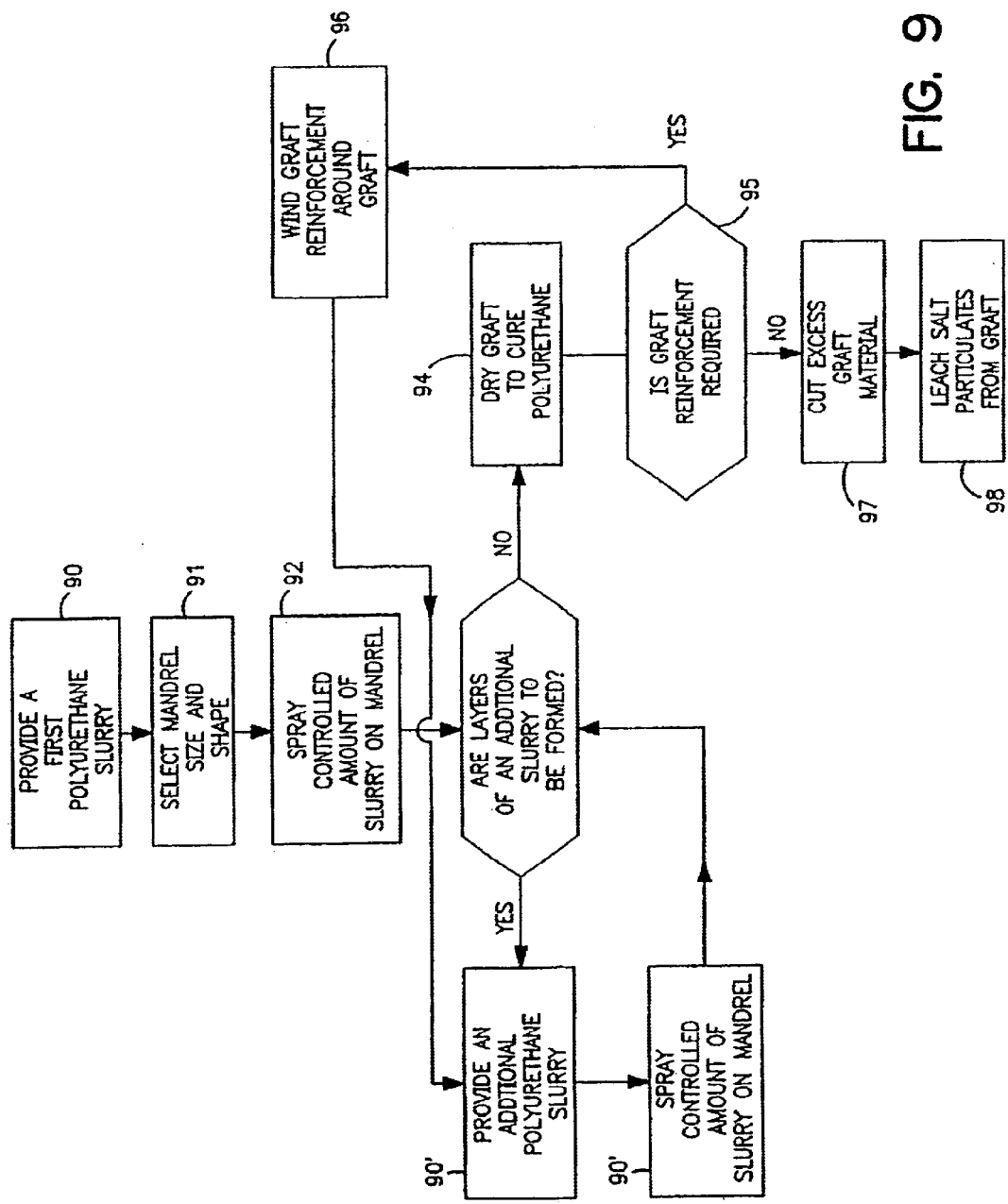
FIG. 9 is a flow chart of another embodiment of a method for forming grafts according to the invention.

Referring to FIG. 9, a flow chart depicts another embodiment of a method for forming grafts according to the invention. In step 90, a first slurry containing a polyurethane composition is provided, and in step 91, a mandrel is selected with a desired size and shape. In step 92, the first slurry may be sprayed onto the mandrel. The spraying may be controlled through the use of masking or by carefully controlling the amount and directing of the sprayed slurry, such that a graft of precisely the desired size and shape may be formed on the mandrel. An advantage of this spraying technique is that it may be more efficient than the dipping or drawing techniques described above and may provide a more uniform coating with less wasted slurry. This process may be repeated until the desired layer thickness is achieved.

In step 93, it is determined whether additional layers of polyurethane are to be applied to the mandrel. If so, in step 90', an additional polyurethane slurry is provided, and in step 92', an additional layer is applied to the mandrel. The thickness of the additional layer(s) may be controlled in the manner described above.

Once the desired layers have been deposited on the mandrel (step 93), the polyurethane layers are dried (e.g., cured) in step 94. If the graft is to be reinforced (step 95), a graft reinforcing member, such as a wire or fiber, may be wound around the graft (step 96), and an additional coating of polyurethane may be applied over the graft reinforcement means (steps 90' and 92'). In step 97, excess graft material may be removed from the graft, and in step 98, salt particles may be leached from the graft to create the desired porous layer(s).

Referring again to FIG. 7a, to form a flared opening which has an axis of the opening which is not parallel to the axis of the graft tube, the flared end is cut at an angle so that the opening is imparted in the desired direction. Grafts, such as CABGs, may be sized to have inner diameters from about two (2) mm to about four (4) mm for the tubular portion of the graft gradually tapering to more than about twice this diameter for the flared opening.

The grafts according to the present invention are multi-layer having an inner layer, which is to be in contact with blood. This layer is a microporous and as all layers are made from preferably a polyether urethane-urea made from condensing MDI, PTMO, and ethylenediamine. The polyurethane preferably is end-capped with dibutylamine. This polyurethane preferably is the base polymer for all three of the layers. Referring again to FIG. 6, the first inner microporous blood contacting layer preferably contains an additive of about 1% to about 5% by weight, which is preferably made by condensing MDI, polydimethylsiloxane and 1,4-butanediol. The first layer preferably may have pores of less than about 38 microns in diameter formed by adding about 1400% sodium chloride particles by weight of polymeric solids to the layer and leaching these particles by exposure to a water bath or a dilute acid bath. The second layer is contiguous with the first inner layer, but will be nonporous, and contain about 1% to about 5% by weight, preferably, about 4.5%, of the same additive. The third and outermost or tissue contacting layer also may be porous and contain the additive. The additive of this layer also may be about 1% to about 5% by weight, preferably, will be about 3.5% by weight of the polymeric solids, and this layer similarly may contain pores of less than about 38 microns in diameter.

In such admixtures, the base polymer is the polymer, whose surface characteristics are modified by the addition of the additive. As noted above, preferably, the surface characteristics are modified to achieve a low surface free energy or a high contact angle of adhesion, or both. Generally, the additive has a significantly lower $\gamma_c$ value than that of the base polymer. The admixture's $\gamma_c$ value may be reduced by dispersing the additive throughout the base polymer. Preferably, the additive is soluble in a solvent and relatively uncrosslinked. Such an additive may be formed into the blood contacting layer (or zone), e.g., first zone 62 in FIG. 6. The additive's surface free energy may be in a range of about 10 to about $35 \times 10^{-5}$ N/cm (about 10 to about 35 dyne/cm). More preferably, its surface free energy is less than about $30 \times 10^{-5}$ N/cm (about 30 dyne/cm), and an optimum surface free energy may be in a range of about 20 to about $25 \times 10^{-5}$ N/cm (about 20 to about 25 dyne/cm).

Alternatively, the porosity of subsequent layers may be somewhat less than that of the first layer. Such subsequent layers may be made by adding about 600% by weight of the polymeric solids of sodium chloride particles to the layer and leaching in a water bath or a dilute acid bath. It will be appreciated that more than three layers may be utilized, e.g,. five, seven, nine, or more layers. The innermost layer preferably is micro-porous, but may be nonporous. If the innermost layer is micro-porous, preferably, there is a non-porous layer contiguous with the micro-porous innermost layer.

The flared end may flare out from the outer diameter of the graft, about three (3) mm out to the maximum diameter of the desired flare, e.g., about twelve (12) mm. In order to impart a flare less than the maximum diameter of the flared end of the mandrel, the mandrel is dipped or drawn into the coating slurry, so that the level of the coating composition only extends up to the portion of the flared mandrel that corresponds to the desired diameter. After the application of each layer, the layer is dried partially to apply the next layer. If the next layer is porous, it will contain salt particles; and after application of the slurry and drying of the graft, the salt particles may be leached out in an aqueous environment. After application of the a final, the spiral reinforcing fiber is applied over the graft and preferably again dipped in or drawn through the slurry to form a polyurethane coating over the wire to secure the wire to the graft. The mandrel then is withdrawn from the graft in the direction of the flare.

Alternatively, the extent of the flared end may be controlled by carefully controlling the spraying of the slurry onto a mandrel. Specifically, the sprayed slurry may be controlled, so that it does not extend beyond a predetermined point on the mandrel. In yet another embodiment, masking may be applied to the mandrel to limit the coverage attained by sprayed polyurethane. Such masking may comprise physical or electromagnetic barriers or shields which prevent the sprayed polyurethane from contacting the surface of the mandrel. Alternatively, the masking may comprise a chemical composition, which repels the polyurethane or prevents it from adhering on the mandrel.

Although the invention has been described with respect to preferred embodiments, the foregoing description and examples are intended to be merely exemplary of the invention. The true scope and spirit of the invention is not intended to be limited by the foregoing description and examples, but instead is intended to be commensurate with the scope of the following claims. Variations and modifications on the elements of the claimed invention will be apparent to persons skilled in the art from a consideration of this specification or practice of the invention disclosed herein.

What is claimed is:

1. A bypass graft comprising:
   a tubular portion configured to extend and to form a conduit between at least a pair of blood vessels and having an internal tubular diameter, a first end, a second end opposite the first end, and a central axis; and
   at least one flared portion having an adjoining end and a compliant flared end formed to facilitate anastomosis, wherein said adjoining end is integrally formed on and is substantially concentric with said second end, and said adjoining end has a diameter not less than said internal tubular diameter, wherein said at least one flared portion comprises an interior surface formed, such that said flared end has a flared end internal diameter, such that said internal flared end diameter is greater than said internal tubular diameter; whereby said at least one flared portion comprises a circumferential skirt adapted for surgical attachment of said graft to one of said blood vessels, wherein said graft is formed without intervening seams or overlap wherein at least said flared portion comprises a plurality of layers.

2. The graft of claim 1, wherein said graft is made from a polymer selected from the group consisting of polyether urethanes, polycarbonate urethanes, polyester urethanes, silicone polyether urethanes, silicone polycarbonate urethanes, and PHMO polyurethanes.

3. The graft of claim 2, wherein said polyether urethane comprises a polyether urethane-urea.

4. The graft of claim 3, wherein said polyether urethane-urea further comprising an additive in the amounts in a range of about 1% to about 5% by weight, said additive formed by condensing a combination of MDI, polydimethylsiloxane, and 1,4-butanediol.

5. The graft of claim 3, wherein said polyether urethane-urea is end-capped with dibutylamine.

6. The graft of claim 1, wherein said graft comprises:
an inner first micro-porous layer of polyether urethane-urea comprising about 1% to about 5% by weight of an additive formed by condensing MDI, polydimethylsiloxane, and 1,4-butanediol;
a second nonporous layer of polyether urethane-urea comprising about 1% to about 5% by weight of said additive; and
a third porous layer of a polyether urethane-urea comprising about 1% to about 5% of said additive.

7. The graft of claim 6, wherein said first layer is contiguous with said second layer.

8. The graft of claim 6, wherein said second layer is contiguous with said third layer.

9. The graft of claim 6, wherein said first layer contains pores having an average diameter of less about 38 microns.

10. The graft of claim 6, wherein said third layer contains pores having an average diameter less than about 38 microns.

11. The graft of claim 1, wherein said flared end has a flared end central axis, which is at an oblique angle to said central axis of said tubular portion.

12. The graft of claim 11, wherein said graft is made a polyether urethane-urea and said polyether urethane-urea further comprises an additive in the amounts in a range of about 1% to about 5% by weight, said additive formed by condensing a combination of MDI, polydimethylsiloxane, and 1,4-butanediol.

13. The graft of claim 1, wherein said circumferential skirt is oriented for attaching at an acute angle to said blood vessel.

14. The graft of claim 13, wherein said graft is made from a polyether urethane-urea and said polyether urethane-urea further comprises an additive in the amounts in a range of about 1% to about 5% by weight, said additive formed by condensing a combination of MDI, polydimethylsiloxane, and 1,4-butanediol.

15. The graft of claim 1, wherein said flared end has a flared end central axis, which is parallel to said central axis of said tubular portion.

16. The graft of claim 15, wherein said graft is made from a polyether urethane-urea and said polyether urethane-urea further comprises an additive in the amounts in a range of about 1% to about 5% by weight, said additive formed by condensing a combination of MDI, polydimethylsiloxane, and 1,4-butanediol.

17. The graft of claim 1 wherein said circumferential skirt is elongated.

18. The graft of claim 17, wherein said graft is made from a polyether urethane-urea and said polyether urethane-urea further comprises an additive in the amounts in a range of about 1% to about 5% by weight, said additive formed by condensing a combination of MDI, polydimethylsiloxane, and 1,4-butanediol.

19. The graft of claim 1, wherein said graft comprises reinforcing member wound around and substantially concentric with said tubular portion.

20. The graft of claim 19, wherein said graft is made from a polyether urethane-urea and said polyether urethane-urea further comprises an additive in the amounts in a range of about 1% to about 5% by weight, said additive formed by condensing a combination of MDI, polydimethylsiloxane, and 1,4-butanediol.

21. The graft of claim 1, wherein said flared end is asymmetrically flared with respect to said central axis of said tubular portion, such that said skirt has a substantially elliptically-shaped circumference.

22. The graft of claim 21, wherein said graft is made from a polymer selected from the group consisting of polyether urethanes, polycarbonate urethanes, polyester urethanes, silicone polyether urethanes, silicone polycarbonate urethanes, and PHMO polyurethanes.

23. The graft of claim 22, wherein said polyurethanes comprise a polyether urethane-urea.

24. The graft of claim 23, wherein said polyether urethane-urea further comprising an additive in the amounts in a range of about 1% to about 5% by weight, said additive formed by condensing a combination of MDI, polydimethylsiloxane, and 1,4-butanediol.

25. The graft of claim 23, wherein said polyether urethane-urea is end-capped with dibutylamine.

26. The graft of claim 21, wherein said graft comprises:
an inner first micro-porous layer of polyether urethane-urea comprising about 1% to about 5% by weight of an additive formed by condensing MDI, polydimethylsiloxane, and 1,4-butanediol;
a second nonporous layer of polyether urethane-urea comprising about 1% to about 5% by weight of said additive; and
a third porous layer of a polyether urethane-urea comprising about 1% to about 5% of said additive.

27. The graft of claim 26, wherein said first layer is contiguous with said second layer.

28. The graft of claim 26, wherein said second layer is contiguous with said third layer.

29. The graft of claim 26, wherein said first layer contains pores having an average diameter of less about 38 microns.

30. The graft of claim 26, wherein said third layer contains pores having an average diameter of less than about 38 microns.

31. A graft of claim 21, wherein said skirt comprises an opening for attaching said skirt at an acute angle to said blood vessel.

32. The graft of claim 21, wherein the flared end comprises an elliptically-shaped opening, which is oriented at an oblique angle to said central axis of said tubular portion.

33. The graft of claim 21, wherein said circumferential skirt is elongated.

34. A method for manufacturing a bypass graft, comprising the steps of:
providing a mandrel having a tubular portion and a flared end bulb with a flared end central axis;
forming at least one layer of polyurethane over said mandrel;
drying said at least one layer of polyurethane, on said mandrel;

forming a skirt edge around said flared end bulb of said mandrel to form an opening at a predetermined angle to said flared end central axis;

forming a second edge around said tubular portion of the mandrel; and removing said graft from said mandrel.

35. The method of claim 34, further comprising the steps of:

providing a first source of polyurethane comprising polymeric solids and sodium chloride particles, such that said sodium chloride particles are in an amount equal to about 1400% by weight of said polymeric solids;

applying a first layer of said source of polyurethane over said mandrel; and leaching said sodium chloride particles from said first layer to form pores.

36. The method of claim 34, further comprising the steps of:

providing a third source of polyurethane comprising polymeric solids and sodium chloride particles, such that said sodium chloride particles are in an amount equal to about 600% by weight of said polymeric solids;

applying a third layer of said third source of polyurethane over said mandrel; and leaching said sodium chloride particles from said third layer to form pores.

37. The method of claim 34, further comprising the steps of:

wrapping said graft with a reinforcing means; and securing said reinforcing means by applying a polyurethane layer thereover.

38. The method of claim 34, wherein the step of forming at least one layer of polyurethane over said mandrel comprises drawing said mandrel through said source of polyurethane.

39. The method of claim 38, wherein the step of forming at least one layer of polyurethane comprises repeatedly drawing said mandrel through said source of polyurethane.

40. The method of claim 34, further comprising the step of forming said skirt edge and controlling a length of said graft by applying a mask to said mandrel to limit exposure of the surface of said mandrel to said source of polyurethane.

41. The method of claim 40, further comprising the step of cutting the flared end of said graft subsequent to removal of said mandrel to impart an asymmetrical opening on said graft.

42. The method of claim 34, wherein the step of forming at least one layer of polyurethane over said mandrel comprises dipping said mandrel into said source of polyurethane.

43. The method of claim 42, wherein the step of forming at least one layer of polyurethane comprises repeatedly dipping said mandrel through said source of polyurethane.

44. The method of claim 42, further comprising the step of controlling a length of said graft by limiting a depth to which said mandrel is dipped into said source of polyurethane.

45. The method of claim 43, further comprising the step of forming said skirt edge and controlling a length of said graft by applying a mask to said mandrel to limit exposure of the surface of said mandrel to said source of polyurethane.

46. The method of claim 42, further comprising the step of cutting the flared end of said graft subsequent to removal of said mandrel to impart an asymmetrical opening on said graft.

47. The method of claim 34, wherein the step of forming at least one layer of polyurethane over said mandrel comprises spraying said source of polyurethane onto said mandrel.

48. The method of claim 47, wherein the step of forming at least one layer of polyurethane comprises repeatedly spraying said source of polyurethane onto said mandrel.

49. The method of claim 47, further comprising the step of forming said skirt edge and controlling a length of said graft by applying a mask to said mandrel to limit exposure of the surface of said mandrel to said source of polyurethane.

50. The method of claim 47, further comprising the step of forming said skirt edge and controlling a length of said graft by directing a sprayed stream of said source of polyurethane onto a selected portion of said mandrel.

51. A bypass graft produced in accordance with the method of claim 34.

52. A bypass graft comprising:

a tubular portion configured to extend and to form a conduit between at least a pair of blood vessels and having an internal tubular diameter, a first end, a second end opposite the first end, and a central axis; and a first flared portion and a second flared portion, each having an adjoining end and a compliant flared end formed to facilitate anastomosis, wherein said adjoining end is integrally formed on and is substantially concentric with said first end and said second end, respectively, and said adjoining end has a diameter not less than said internal tubular diameter, wherein each of said flared portions comprises an exterior surface formed, such that said flared end has a flared end internal diameter, such that said internal flared end diameter is greater than said internal tubular diameter; whereby each of said flared portions comprises a circumferential skirt adapted for surgical attachment of said graft to one of said blood vessels, wherein said graft is formed without intervening seams or overlap wherein each of at least said flared portions comprises a plurality of layers.

* * * * *